(12) United States Patent
Schmidt et al.

(10) Patent No.: US 6,294,710 B1
(45) Date of Patent: Sep. 25, 2001

(54) FLUID DISTRIBUTION MATERIALS WITH IMPROVED WICKING PROPERTIES

(75) Inventors: Mattias Schmidt, Idstein; Vincenzo D'Acchioli, Kelkheim, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/194,253

(22) PCT Filed: May 28, 1997

(86) PCT No.: PCT/US97/09124

§ 371 Date: Nov. 25, 1998

§ 102(e) Date: Nov. 25, 1998

(87) PCT Pub. No.: WO97/45087

PCT Pub. Date: Dec. 4, 1997

(30) Foreign Application Priority Data

May 28, 1996 (EP) ................................................ 96108427

(51) Int. Cl.⁷ ...................................................... A61F 13/46
(52) U.S. Cl. .......................... 604/378; 604/365; 604/366; 604/367; 604/369; 604/370; 604/372; 604/383
(58) Field of Search ..................................... 604/366, 369, 604/365, 367, 370, 372, 378, 383

(56) References Cited

U.S. PATENT DOCUMENTS

| | | | |
|---|---|---|---|
| H1511 | 12/1995 | Chappell et al. | 604/383 |
| 3,575,174 | 4/1971 | Mogor | 128/290 |
| 3,952,745 | 4/1976 | Duncan | 128/287 |
| 4,440,597 | 4/1984 | Wells et al. | 162/111 |
| 4,578,068 | 3/1986 | Kramer et al. | 604/368 |
| 4,781,710 | 11/1988 | Megison et al. | 604/378 |
| 4,898,642 | 2/1990 | Moore et al. | 162/157.6 |
| 5,117,540 | 6/1992 | Walton et al. | 26/18.6 |
| 5,244,482 | 9/1993 | Hassenboehler, Jr. et al. | 55/528 |
| 5,268,224 | 12/1993 | DesMarais et al. | 428/286 |
| 5,360,420 | 11/1994 | Cook et al. | 604/378 |
| 5,549,589 | 8/1996 | Horney et al. | 604/366 |
| 5,800,416 | 9/1998 | Seger et al. | 604/366 |

FOREIGN PATENT DOCUMENTS

| | | |
|---|---|---|
| 0 343 941 A2 | 11/1989 | (EP) . |
| 0 397 110 A2 | 11/1990 | (EP) . |
| 0 640 330 A1 | 3/1995 | (EP) . |

*Primary Examiner*—John G. Weiss
*Assistant Examiner*—Michael Bogart
(74) *Attorney, Agent, or Firm*—Eileen L. Hughett; Edward J. Milbrada; T. David Reed (57) ABSTRACT

The present invention relates to the selection of materials which are particularly useful as fluid distribution material for being used in disposable absorbent articles by being characterized in that they have a wicking time of less than 120 seconds and a cumulative flux of more than 0.075 grams/cm2/second for said preferential fluid distribution direction at 12.4 cm height, when applying the Vertical Wicking Test. A further useful selection criteria for such materials is a non-isotropic fluid distribution behavior, expressed in that the wicking time in the preferential distribution direction is less than 80% of the wicking time of perpendicular direction at 8.3 cm height, when applying the same test.

21 Claims, 4 Drawing Sheets

FLUID DISTRIBUTION MATERIALS WITH IMPROVED WICKING PROPERTIES

FIELD OF THE INVENTION

The present invention relates to fluid distribution materials with improved wicking properties in a preferential fluid distribution direction. Such fluid distribution members are particularly useful in absorbent core structures such as used in disposable absorbent articles like baby diapers, incontinence products or catamenial products.

BACKGROUND OF THE INVENTION

In the general field of disposable absorbent articles and structures, materials exhibiting specific fluid distribution properties are well known. Such materials became more and more relevant with the introduction of highly absorbent materials, also called Absorbent gelling materials or superabsorber, which do provide a good means for storing aqueous fluids such as urine, but do not enhance fluid transport, and even reduction of fluid transport can occur when sub-optimal designs and/or suboptimal materials are employed, and phenomena often referred to as "gel-blocking" take place. For example, in structures where the superabsorbent is homogeneously mixed with cellulose fibres, a certain critical concentration, which is strongly depending on the choice of the superabsorbent material, should not be exceeded in order to not deteriorate efficacy of the absorbent core.

As a consequence, a vast number of absorbent core designs have appeared with a separated functionality of storage and fluid distribution. This can be exemplified by EP 0 397 110 (Latimer) disclosing an absorbent article comprising a surge management portion for improved fluid handling, having specific basis weights, acquisition times and residual wetness; U.S. Pat. No. 4,898,642 of Moore et al. discloses specially twisted, chemically stiffened cellulosic fibres and absorbent structures made therefrom; EP0 640 330 (Bewick-Sonntag et al.) discloses the use of such fibres in a specific arrangement with specific superabsorbent materials. EP 0 397 110 (Latimer) discloses an absorbent article comprising a surge management region for improved fluid handling, having specific basis weights, acquisition times and residual wetness.

Initially, the requirements for a distribution material were not very high, and standard paper tissue materials such as used as wrapsheets for the cores and described for example in U.S. Pat. No. 3,952,745 (Duncan), were applied to also enhance the fluid distribution, as described in EP-0 343 941 (Reising) or U.S. Pat. No. 4,578,068 (Kramer).

As some of these materials did exhibit an undesired hard feel, methods for post formation treatments were well known to improve softness. "Post formation treatment" refers to the fact that—instead of, or, in addition to increasing softness during the making or formation of the tissue—the tissue is treated mechanically in a separate process step after forming and drying of the tissue, often just prior to further processing such as combining the tissue with other materials to form an absorbent core or article. Examples for such treatments are U.S. Pat. No. 5,117,540 (Walton) or U.S. Pat. No. 4,440,597 (Wells).

With the wish to improve the functionality of the absorbent articles, more specific requirements for distribution materials developed, such that porous materials were investigated in more depth. Examples are cellulosic foams such as commercially available by Spontex SA. France or High Internal Phase polymerized materials such as described in U.S. Pat. No. 5,268,224 (DesMarais). In order to improve the longitudinal fluid distribution, high surface area synthetic fibres were applied in absorbent structures, such as described in US Statutory Invention Registration H1511.

These approaches have in common, that they are complex to manufacture and hence relatively expensive when compared to cellulosic fibre-based materials.

Hence, early approaches aimed at improving the wicking properties of cellulose fibre-based materials, such as U.S. Pat. No. 3,575,174 or U.S. Pat. No. 4,781,710, whereby parts of the structure are compressed to a higher density, thus creating smaller pores for increased wicking height, for example, along "wicking lines" or in closed mesh patterns. Such attempts also aimed at achieving a certain preferential fluid distribution direction. However, in these approaches the size of the large pores was reduced relatively more than of the smaller pores, such that the positive impact of the increased wicking height was counterbalanced by reduced amount of fluid which could be transported to such heights.

Other attempts to impact on the pore size of distribution materials is described in U.S. Pat. No. 5,244,482 (Hassenboehler), aiming at reducing maximum pore size by stretching a fibrous structure comprising meltable fibres in one direction and "freezing" the deformation by heat curing.

Also, special material composites were developed, aiming at allowing to tailor the pore size and pore size distribution. Examples for such improvements are described in greater detail in commonly-assigned, co-pending (allowed) U.S. patent application Ser. No. 08/382,817, filed Feb. 3, 1995 in the names of Horney et al., entitled "Fluid Distribution Member for Absorbent Articles Exhibiting High Suction and High Capacity", or in commonly-assigned, co-pending U.S. patent application Ser. No. 08/633,630, filed Apr. 17, 1996 in the names of Seger et al., entitled "High Capacity Fluid Absorbent Members". Both aim essentially at providing a resilient structure by using specially stiffened cellulosic fibres such as crosslinked cellulose soft-wood fibres, and by filling the large pores with small and thin cellulosic fibres such as eucalyptus fibres. Both applications further add means for providing sufficient integrity and strength to the structure, the first one (U.S. Ser. No. 08/382,817) by adding thermoplastic fibres and partially melting these, the second (U.S. Ser. No. 08/633,630) by adding a chemical binder.

However, it has been realised, that in spite of more complex technologies, all modifications are still limited by the inverse relationship of wicking height and wicking flux, i.e., wicking height can be increased, but at cost of reduced wicking flux. There has been no recognition of the ability to improve both at the same time.

Surprisingly, the inventors have been able to overcome this incompatibility by carefully selecting the criteria to assess materials and thus identifying the appropriate materials to satisfy these characteristics.

Hence the present invention is concerned with providing these selection criteria to be able to identify materials which both improved wicking height and flux.

A further object of the present invention are materials with both increased wicking height and flux at the same time.

A further object of the invention are materials with improved directionality of transport properties, especially in the length (often also called machine) direction of the web.

Still a further object of the present invention is to provide absorbent articles comprising such materials.

SUMMARY OF THE INVENTION

Surprisingly, it has been found that it is possible to select materials which are particularly useful as fluid distribution material by having one preferential fluid distribution direction and being characterised in that they have a wicking time of less than 120 seconds and a cumulative flux of more than 0.075 grams/cm2/second for said preferential fluid distribution direction at 12.4 cm height, when applying the vertical wicking test as described below.

A further useful selection criteria for such materials is a non-isotropic fluid distribution behaviour, expressed in that the wicking time in the preferential distribution direction is less than 80% of the wicking time of perpendicular direction at 8.3 cm height, when applying the same test.

Such selection criteria have been applied to various materials, whereby one class of distribution materials, which have been submitted a special mechanical post-formation treatment, have shown particularly good results.

DETAILED DESCRIPTION OF THE INVENTION

Fluid distribution materials in the context of the present invention are materials for applications such as in absorbent articles, which are intended to support the fluid transport mechanisms in such articles. Such articles generally have two centerlines, a longitudinal and a transverse one. The term "longitudinal" as used herein, refers to a line axis or direction in the plane of the article, that is generally aligned with (e.g. approximately parallel to) a vertical plane which bisects a standing wearer of such an article into left and right body halves. The fluid transport mechanisms may then be required to effectively use absorbent material which can be spread in the article over a larger region than the loading regions, i.e. the region of the articles where bodily discharges are disposed onto the surface of the absorbent article. Such transport can occur through driving forces such as gravity, which will not allow fluid distribution against the direction of the gravity, and hence often not satisfy requirements as set out for absorbent articles, whereby fluid needs to be transported from the loading point, where discharged fluids are discharged onto the absorbent article, to other parts of the article, which are positioned "higher", i.e. upwards against the direction of gravity.

This wicking is generally achieved by exploiting capillary forces, and can be best assessed by testing the materials in the vertical orientation, i.e., positioning these along the direction of gravity.

Vertical Wicking

A key functionality of the materials according to the present invention is the combination of increased wicking height and flux.

As absorbent articles can have significant dimensions due to the anatomy of the wearer and the dimensions of the absorbent article, the ability of wicking high up is important, and vertical wicking distances such as 12.4 cm (5 inch) or 8.3 cm (3.3 inch) can be typical for realistic conditions.

Equally important is the amount of fluid which has to be transported. Characteristic loadings for baby diapers can be more than 300 ml of urine loading, in voidings often at 75 ml per voiding, and voiding rates of up to 15 ml/sec. Hence the need for the ability to transport significant amounts becomes obvious. There is, however, a further need for low material usage both due to economical use of materials and due to comfort and fit requirements for the wearer. Hence, materials are required to allow transport of large amounts of fluids in short times through a small cross section of such material. This can generally be expressed by the "vertical wicking flux" parameter, being defined by the cumulative amount of fluid being transported to a given height through a certain cross-section of material in a certain time, expressed in $g/cm^2/sec$ [ml/cm2/sec], and by the time the fluid front penetrates up to a certain height in the material against gravity.

These parameters can be most easily determined by using the vertical wicking test, such as specified below, measuring the ability of a material to transport fluid through its internal voids (such as pores) at constancy or absence of external forces, such as gravity or centrifugal forces. Essentially, a specimen of the material is placed in a vertical position extending out of a fluid reservoir. The transport against the gravity can be monitored by measuring both the upward movement of the wetting front and the amount of fluid which is picked up by the material.

Wicking height can be easily increased by decreasing the effective pore size of the distribution material, according to the generally known Lucas-Washburn relationship for capillary systems, which often has also been applied to approximate porous systems. For a given fluid—be this urine or menstrual fluid—and a certain material exhibiting a certain surface energy, the required capillary (or pore) diameter can be approximated to allow wicking up to a certain required height.

Obviously, when aiming for large wicking heights, this relation requires small capillary diameter.

However, such small capillaries are not able to handle high amounts of fluid, and the cumulative flux for such fluids through such a material with small pores is significantly reduced. This is caused by the high internal friction (or low permeability) that is linked to small pores (according to the Hagen-Poisseuille relationship).

Thus, whilst conventional materials exhibit either large heights combined with low flux or large flux values at low heights, it has been found that this trade off can be overcome such as by materials described further below, and providing fast wicking of less than 120 seconds and more preferably less than 50 seconds to a relatively large height of 12.4 cm, and at the same time large flux of at least 0.075 g/sec/cm2, preferably more than 0.12 g/cm2/sec and even more preferably more than 0.25 g/sec/cm2.

Preferential Wicking Direction

Beyond the effect of high wicking flux to high wicking heights, it is a further aspect of distribution materials according to the present invention to have a pronounced preferential fluid transport direction, i.e., fluid transport in one direction is better than in the others.

In order to explain this in more detail, the following Cartesian coordinate system with three perpendicular axes x, y, and z will be used and explained for a sheet like roll-good (like conventional tissues, or nonwoven):

The length of the roll is the x-direction. Often, this is also referred to as the "machine direction" of the web.

The thickness is defined as z-direction.

The remaining axis (often also called "cross direction") is the y-direction.

Because of the above mentioned anatomical requirements and desire to provide well fitting and comfortable absorbent articles, such articles—and also the absorbent cores comprised in such structures—have generally an elongated shape, i.e. they are longer than they are wide, and—compared to these two dimensions—relatively thin. In many cases, the absorbent material is arranged along the full length of the absorbent, such that it is desired to have the fluid transported effectively along the length dimension of this article to spread it across the full article and make effective use of absorbent material in the regions more remote from the loading point. At the same time, "cross-directional" transport in y-direction of the material is less desired, as there is a risk of liquid leaking at the side of the article, often in spite of gasketing means such elastic bands or secondary leg cuffs.

Thus the liquid transport should be preferentially in x-direction when compared to y-direction.

Also, in many designs, fast z-directional transport is not desired, in order to not prematurely over saturate the fluid storage capacity around the loading point, but to rather allow spreading of the fluid across the full area of the article.

Comparative materials already exhibit a certain non-isotropic fluid distribution behaviours; e.g., EP-0 548 714 (Serbiak) is describing absorbent materials, for which upon loading in an horizontal position the wetting stains tend not to be circular, but spread in one preferred direction more than in the other. This horizontal spreading, however, is a different mechanism than wicking, as it is dominated by gravity driven "free flow" essentially "flooding" the structure though large (and preferentially not collapsing) pores or voids, which exhibit low capillary forces.

However, it has been found, that for distribution materials whereby the transport is based upon wicking mechanism, this spreading ratio is not sufficient to provide good performance, but that non-isotropic behaviours are desired also for vertical wicking, namely both for wicking height and cumulative flux. Hence, such material properties are a special aspect of the invention. It could be observed, that preferred materials as described below have significantly reduced wicking times in the y directional wicking compared to the x-directional wicking.

Fluid Distribution Materials

Without wishing to be bound by this theory, it is believed that in order to achieve the novel effect of combining superior performance of improved wicking height and high wicking flux, materials have to satisfy certain general requirements, namely not only specific pore sizes or pore shapes, but also a specific arrangement of the pores relative to each other, i.e., a non-random arrangement or pores of different size and shape.

When the distribution materials will be used to transport essentially aqueous fluids (such as urine or menses) it is desirable, that the materials exhibit a certain hydrophilicity.

This, however does not mean, that these have to be completely hydrophilic (i.e. have a wetting angle for water of approximately zero), nor that this hydrophilicity has to be uniformly across all surfaces in all regions.

Generally, hydrophilicity can be achieved by starting from hydrophilic base materials, such when using cellulosic fibres, or polymeric material—which mostly are relatively hydrophobic—with resin incorporated or surface applied surfactants. Alternatively, the distribution material itself can further be hydrophilicised as such, e.g., after forming a web comprising hydrophobic materials, this can be rendered hydrophilic by addition of surfactants.

A specific aspect of the invention relates to the modification of conventional materials such as to then satisfy the requirements as laid out in the above.

Such conventional materials generally have due to their formation process a random arrangement of pores with different size and shape. An appropriate post-formation treatment can be applied to modify the pore size, shape, and respective arrangement. Additionally, in order to be suitable for such a post-formation treatment, these materials must be plastically deformable, i.e. must neither be too brittle to break upon deformation, nor too elastic to immediately "spring back" to the pre-modification pore sizes/shapes etc.

Whilst many porous materials are contemplated to be suitable for materials according to the present invention, particularly preferred materials are fibrous wet-laid webs comprising a first fibre type which is resilient for mechanical deformation;

a second fibre type exhibiting a large surface to mass ratio;

and a bonding agent.

First, Resilient Fibre Type

A wide variety of resilient fibres can be envisaged to perform well in materials according to the present invention. Apart from well known synthetic fibres such as being based on polyethyleneterephatalate, polyester, polyamine, resilient polyolefins or combinations thereof e.g., in bi-component fibre form, a particularly preferred fibre is a chemically-stiffened, twisted bulking cellulosic fibre. As used herein, the term "chemically stiffened, twisted, and curled fibres" means any fibres which have been stiffened by chemical means to increase stiffness of the fibres under both dry and aqueous conditions. Such means include the addition of chemical stiffening agents which, for example, coat and/or impregnate the fibres. Such means also include the stiffening of the fibres by altering the chemical structure of the fibres themselves, e.g., by cross-linking polymer chains.

Fibres stiffened by crosslink bonds in individualised (i.e., fluffed) form are disclosed, for example, in Bernardin, U.S. Pat. No. 3,224,926, Issued Dec. 21, 1965; Chung, U.S. Pat. No. 3,440,135, Issued Apr. 22, 1969; Chatterjee, U.S. Pat. No. 3,932,209, Issued Jan. 13, 1976 and Sangenis et al., U.S. Pat. No. 4,035,147, Issued Jul. 12, 1977. More preferred fibres are disclosed in Dean et al., U.S. Pat. No. 4,822,453, issued Apr. 18, 1989, Dean et al., U.S. Pat. No. 4,888,093, issued Dec. 19, 1989, and Moore et al., U.S. Pat. No. 4,898,642, issued Feb. 6, 1990.

Without wishing to be bound by theory, in addition to being hydrophilic, these stiffened fibres are preferably substantially "hornified". Thus, the cell walls do not swell appreciably and maintain the void volume within the network when wetted. Chemically stiffened, twisted, and curled cellulosic fibres provide permeability, flexibility, and increased hydrophilicity.

For exemplary purposes, other polymeric stiffening agents which can coat or impregnate cellulosic fibres include: cationic modified starch having nitrogen-containing groups (e.g., amino groups) such as those available from National Starch and Chemical Corp., Bridgewater, N.J., USA; latex; wet strength resins such as polyamide-epichlorohydrin resin (e.g., Kymene™ 557H, Hercules, Inc. Wilmington, Del. USA), polyacrylamide resin (described, for example, in U.S. Pat. 3,556,932 issued Jan. 19, 1971 to Coscia, et al.; also, for example, the commercially available polyacrylamide marketed by Cytec Industries, West Patterson, N.J., USA, under the trade name Parez ™ 631 NC); urea formaldehyde and melamine formaldehyde resins, and polyethylenimine resins. A general dissertation on wet strength resins utilised in the paper art, and generally applicable herein, can be found in TAPPI monograph series No.29. "Wet Strength in Paper and Paperboard", Technical Association of the Pulp and Paper Industry (New York, 1965).

The fibres utilised in the fluid absorbent members herein are preferably stiffened by means of chemical reaction. For example crosslinking agents can be applied to the fibres which, subsequent to application, are caused to chemically form intra-fibre crosslink bonds. These crosslink bonds can increase stiffness of the fibres. Whereas the utilisation of intrafibre crosslink bonds to chemically stiffen the fibres is preferred, it is not meant to exclude other types of reactions for chemical stiffening of the fibres.

In the more preferred stiffened fibres, chemical processing includes intrafiber crosslinking with crosslinking agents while such fibres are in a relatively dehydrated, defibrillated (i.e., individualised), twisted, curled condition. Suitable chemical stiffening agents include monomeric crosslinking agents including, but not limited to, $C_2$–$C_8$ dialdehydes and $C_2$–$C_8$ monoaldehydes having an acid functionality can be employed to form the crosslinking solution. These compounds are capable of reacting with at least two hydroxyl groups in a single cellulose chain or on approximately located cellulose chains in a single fibre. Such crosslinking agents contemplated for use in preparing the stiffened cellulose fibres include, but are not limited to, glutaraldehyde, glyoxal, formaldehyde, and glyoxylic acid. Other suitable stiffening agents are polycarboxylates, such as citric acid. The polycarboxylate stiffening agents and a process for making stiffened fibres from them are described in U.S. Pat. No. 5,190,563, issued Mar. 2, 1993. The effect of crosslinking under these conditions is to form fibres which are stiffened and which tend to retain their twisted, curled configuration during use in the absorbent articles herein. Such fibres, and processes for making them are described in the above incorporated patents.

Stiffened cellulose fibres herein having the preferred physical and performance characteristics herein before set forth, can be prepared by internally crosslinking such fibres in relatively dehydrated form while or after such fibres are being or have been dried and defibrated (i.e., "fluffed") as described in U.S. Pat. No. 4,898,642. It is not, however, meant to necessarily exclude other hydrophilic, chemically stiffened, twisted, and curled fibres from this invention, such other fibres being described in (but, not limited to) the previously mentioned U.S. Pat. Nos. 3,224,926, 3,440,135, 4,035,147, and 3,932,209. Other non-chemical means of providing stiffened, twisted, and curled cellulose fibres are also contemplated as being within the scope of the present invention, such as high consistency (generally greater than about 30%) mechanical treatment (e.g., frotapulping and/or refining, etc.). Such methods are described in greater detail in U.S. Pat. Nos. 4,976,819 and 5,244,541, issued Dec. 11, 1990 and Sep. 14, 1993, respectively, to Mary L. Minton and entitled "Pulp Treatment Methods".

Second, High Surface Area Type Fibres

Fluid distribution materials according to the present invention further comprise a high surface fibre to provide capillary pressure (or suction) to the fluid absorbent member. These high surface area fibres are generally small and highly conformable. They provide the substrate with capillary pressure well in excess of the capillary pressure found in the bulk-providing chemically stiffened, twisted, and curled fibres (unrefined) alone.

Whilst also synthetic fibres such as having a very small diameter ("microfibres") or having a special surface configuration are contemplated to be suitable, a presently preferred fibre for this high surface application is the eucalyptus family of wood pulp fibres. Eucalyptus provides desirable capillary pressure characteristics in combination with the chemically stiffened, twisted, and curled fibres and will not easily pass through the forming screen, as does a significant amount of the cellulose fines described below. Particularly suitable eucalyptus fibres include those of the eucalyptus grandis species.

Other suitable surface area generating fibres for addition to the stiffened cellulosic fibres prior to formation of the wet web from a pulp slurry include, but are not limited to, a variety of cellulosic and synthetic fibrous materials such as those disclosed in U.S. Pat. No. 5,217,445, issued to Young et al. on Jun. 8, 1993. Such materials include nonstiffened cellulosic fibres (i.e., conventional cellulosic pulp fibres), highly refined, stiffened and nonstiffened, cellulosic fibres referred to herein as "crill", and high surface area cellulosic material such as expanded cellulose fibres (hereinafter described). The high surface area cellulose is well mixed with the stiffened fibres in slurry and the slurry is wetlaid. A blender, a repulper, a deflaker, a valley beater, a refiner (e.g., single, cone, or double disk refiner), or other equipment known in the art, can be used to mix, declump, or refine the stiffened fibres and high surface area cellulose.

High surface area cellulose can also be made from cellulosic fibres by passing a liquid suspension of cellulose fibres through a small diameter orifice, in which the suspension is subjected to a pressure drop of at least 4.3 Pa (3000 psig) and a high velocity shearing action, followed by a high velocity decelerating impact. Passage of the suspension through the orifice is repeated until a substantially stable suspension is obtained. See U.S. Pat. No. 4,483,743, Turbak et al., Nov. 20, 1984.

Binding Means

Relative to conventional non-stiffened cellulosic fibres, the crosslinked, twisted, stiffened fibres in combination with high surface area fibres described above form lower tensile strength sheets, particular in a wet condition. Therefore, in order to facilitate processing and provide product-specific mechanical properties, in both wet and dry states, a binding means is preferably integrally incorporated into or onto the web. This can be done by adding the binding means to pulp prior to web formation, by applying the binding means to a wetlaid web after deposition on a forming wire, and before drying, after drying, or a combination thereof.

Whilst the specific bindings means to provide this certain strength to the formed web is believed to not be critical to the fluid handling performance, thermoplastic fibres have been found to provide a preferred option, and a chemically bound web an even more preferred execution.

When using thermoplastic fibres, these form a thermally bonded polymer micro web in the material, whereby the polymer bonding fibres (such as Hoechst-Celanese Copolyolefin Bicomponent fibre and the like) strongly bonding at fibre intersections. This polymer micro structure allows the web to survive the softening processes. The thermally set polymer micro web properties significantly control and maintain the wet/dry tensile, flexibility, and resiliency, thus permitting extensive mechanical treatment while maintaining acceptable wet/dry tensile strength and resiliency.

In an preferred execution, the fluid distribution material comprises a wetlaid web of stiffened cellulosic fibres wherein the web is reinforced with between about 0% to about 50%, preferably between about 5% to about 25%, more preferably between about 7% to about 15%, of a thermoplastic binding material, wherein the thermoplastic binding material provides bond sites at intersections of the binding fibres with either other binding fibres, chemically stiffened, twisted, and curled cellulosic fibres, or high surface area fibres. Such thermally bonded webs can, in general, be made by forming a web comprising the stiffened cellulosic fibres and thermoplastic fibres, which are preferably evenly distributed throughout. The thermoplastic fibrous material can be intermixed with the stiffened cellulosic fibres and fine fibres in the aqueous slurry prior to web formation. Once formed, the web is thermally bonded by heating the web until the thermoplastic portion of the fibres melt. Specific non-limiting examples of suitable fibrous materials include polyester hot melt fibres (KODEL 410), bicomponent fibres, tricomponent fibres, mixtures thereof, and the like.

In addition, a crimped type polymer-based binder fibre will contribute added bulk to the web. A presently preferred polymer-based binder fibre of the crimped variety is Hoechst-Celanese Copolyolefin Bicomponent fibre, commercially available under the tradename CELBOND® from Hoechst Celanese Corporation, type 255, lot 33865A, having a dTex of about 3.3, a denier of about 3.0, and a fibre length of about 6.4 mm.

The thermoplastic binding materials useful for the fluid distribution members herein also include any hot melt adhesive which can be melted at temperatures which will not extensively damage the cellulosic fibres. Preferably, the melting point of the thermoplastic binding material will be less than about (175° C.), preferably between about 75° C. and about 175° C. In any case, the melting point should be no lower than temperatures at which the articles of this invention are likely to be stored, whereby melting point will be typically no lower than about 50° C.

The thermoplastic binding material may, for example, be polyethylene, polypropylene, polyester, polyvinyl chloride, polyvinylidene chloride. Preferably, the thermoplastic fibres will not significantly imbibe or absorb aqueous fluid. However, the surface of the thermoplastic material can be hydrophilic or hydrophobic. (As used herein, the terms "hydrophilic" and "hydrophobic" shall refer to the extent to which the surfaces are wetted by water.) Hydrophilic material becomes more preferred at higher thermoplastic levels, particularly at levels above about 40%.

Thermoplastic fibres for use herein can be on the order of about 0.1 cm to about 6 cm long, preferably from about 0.3 cm to about 3.0 cm.

The thermoplastic is preferably melted by through-air bonding, however, other methods such as infra red light, steam drum drying, Yankee, etc., are not meant to be excluded. In another variation, the web is subjected to heat embossing on one or both faces of the web. This technique is described in further detail in U.S. Pat. No. 4,590,114.

As discussed previously, scrims such as tissue sheets and other water pervious nonwoven sheets can be used as external support in addition to or in place of the binding means described above.

An even preferred starting material comprises chemical binders. The chemically bonded web properties significantly control and maintain the wet/dry tensile, flexibility, and resiliency, permitting extensive mechanical treatment after the web formation step, while maintaining acceptable wet/dry tensile strength and resiliency.

Such chemical additive binding means for increasing physical integrity of the absorbent member and/or facilitating processing of webs, especially wetlaid webs, can be resinous binders, latex, and starch known in the art for providing increased integrity to fibrous webs. Suitable resinous binders include those which are known for their ability to provide wet, dry, or both wet and dry strength in paper structures, such as can be found in TAPPI monograph series No. 29, Wet Strength in Paper and Paperboard, Technical Association of the Pulp and Paper Industry (New York, 1965). Suitable resins include polyamide-epichlorohydrin and polyacrylamide-glyoxal resins. Other resins finding utility in this invention are urea formaldehyde and melamine formaldehyde resins. The more common functional groups of these polyfunctional resins are nitrogen containing groups such as amino groups and methylol groups attached to nitrogen. Polyethylenimine type resins may also find utility in the present invention. A presently preferred chemical additive binding means is the commercially available polyacrylamide-glyoxal resin marketed by Cytec Industries, West Patterson, N.J., USA, under the trade name Parez™ 631 NC. Starch, particularly cationic, modified starches may also find utility as chemical additives in the present invention. Such cationic starch materials, generally modified with nitrogen containing groups such as amino groups and methylol groups attached to nitrogen, may be obtained from National Starch and Chemical Corporation, located in Bridgewater, N.J. Other suitable binders include, but are not limited to, polyacrylic acid, polyvinyl alcohol, polyvinyl acetate.

The level of chemical additive binders which are added will typically be from about 0% to about 5% total web weight basis. Chemical additive binders which are hydrophilic, however, can be utilised in larger quantities. If the chemical binder additives are added to the stiffened fibres in aqueous slurry, conventional, nonstiffened cellulosic fibres or high surface area cellulose is preferably also present, to enhance retention of the chemical additive binder. Chemical additive binders can be applied to dried or undried webs by printing, spraying, or other methods known in the art.

In addition to the use of a chemical binding means, fluid distribution materials may also benefit from the integration of a thermally bonded polymer micro web in the material as explained above.

Material Formation Process.

The constituent components of the preferred starting materials for fluid distribution materials according to the present invention may be blended together and formed into webs by a variety of methods, including wet-laying methods, air-laying methods, carding, and other methods, of which wet-laying methods are presently preferred.

Techniques for wetlaying cellulosic fibrous material to form sheets such as dry lap and paper are well known in the art. These techniques are generally applicable to the wet-laying of the stiffened fibres to form wetlaid sheets useful in the absorbent structures of this invention. Suitable wetlaying techniques include handsheeting, and wetlaying with the utilisation of paper making machines as disclosed, for instance, by L. H. Sanford et al. in U.S. Pat. No. 3,301,746. Due to the behaviour of chemically stiffened, twisted, and curled fibres, particularly their tendency to flocculate in aqueous slurries, certain processing modifications, hereafter described, are preferably implemented when wetlaying with paper making machines.

In general, wetlaid webs can be made by depositing an aqueous slurry of fibres on to a foraminous forming wire, dewatering the wetlaid slurry to form a wet web, and drying the wet web. Preferably, the aqueous slurries of fibres for wetlaying will have a fibre consistency of between about 0.02% and about 2.0%, preferably between about 0.02% and about 0.2%, total slurry weight basis. Deposition of the slurry is typically accomplished using an apparatus known in the art as a headbox. The headbox has an opening, known as a slice, for delivering the aqueous slurry of fibres onto the foraminous forming wire. The forming wire can be of construction and mesh size used for dry lap or other paper making processing. Conventional designs of headboxes known in the art for drylap and tissue sheet formation may be used. Suitable commercially available headboxes include, for example, open, fixed roof, twin wire, inclined wire, and drum former headboxes.

Once formed, the wet web is dewatered and dried. Dewatering can be performed with foils, suction boxes, or other vacuum devices or gravitational flow. Typically, dewatering increases the fibre consistency to between about 8% and about 30%, total wet web weight basis, preferably between about 8% and about 23%. Dewatering to consistencies above about 23% may require wet-pressing and is less preferred. After dewatering, the web can be, but is not necessarily, transferred from the forming wire to a drying fabric which transports the web to drying apparatuses.

Drying of the wet web may be accomplished utilising many techniques known in the art. When thermoplastic binding materials are included in the web, is particularly important that the web be dried thoroughly and uniformly at a temperature which fuses the thermoplastic binding material to other fibrous materials, but not so high as to cause the thermoplastic binding material to flow into the void volume of the network. Drying can be accomplished via, for example, a thermal blow-through dryer, a thermal air-impingement dryer, and heated drum dryers, including Yankee dryers. The wetlaid webs are preferably dried to completion (generally to fibre consistencies between about 95% to about 99%). The flexibility of the fully dried web is preferably increased such as by techniques well known in the art such as creping the web using a Yankee dryer with a doctor blade.

In addition to preferred wetlaying processes of the types described above, under some circumstances it may be desirable to form fluid absorbent members according to the present invention by airlaying, carding, or other suitable methods.

Post Formation Treatment

In order to achieve the required properties according to the present invention, the prior art materials as discussed above are subjected to a special process step. Similar processes have been developed for treating stretch laminate materials and are described in U.S. Pat. No. 5,167,897 (Weber) relating to stretch materials or in co-filed application relating to a process for treating fluid distribution materials.

Essentially, this process provides mechanical treatment of the web, by feeding the starting material through at least two rolls each with circumferential ridges and grooves, which are run at such a close tolerance that the web undergoes permanent deformation.

Figure 1:
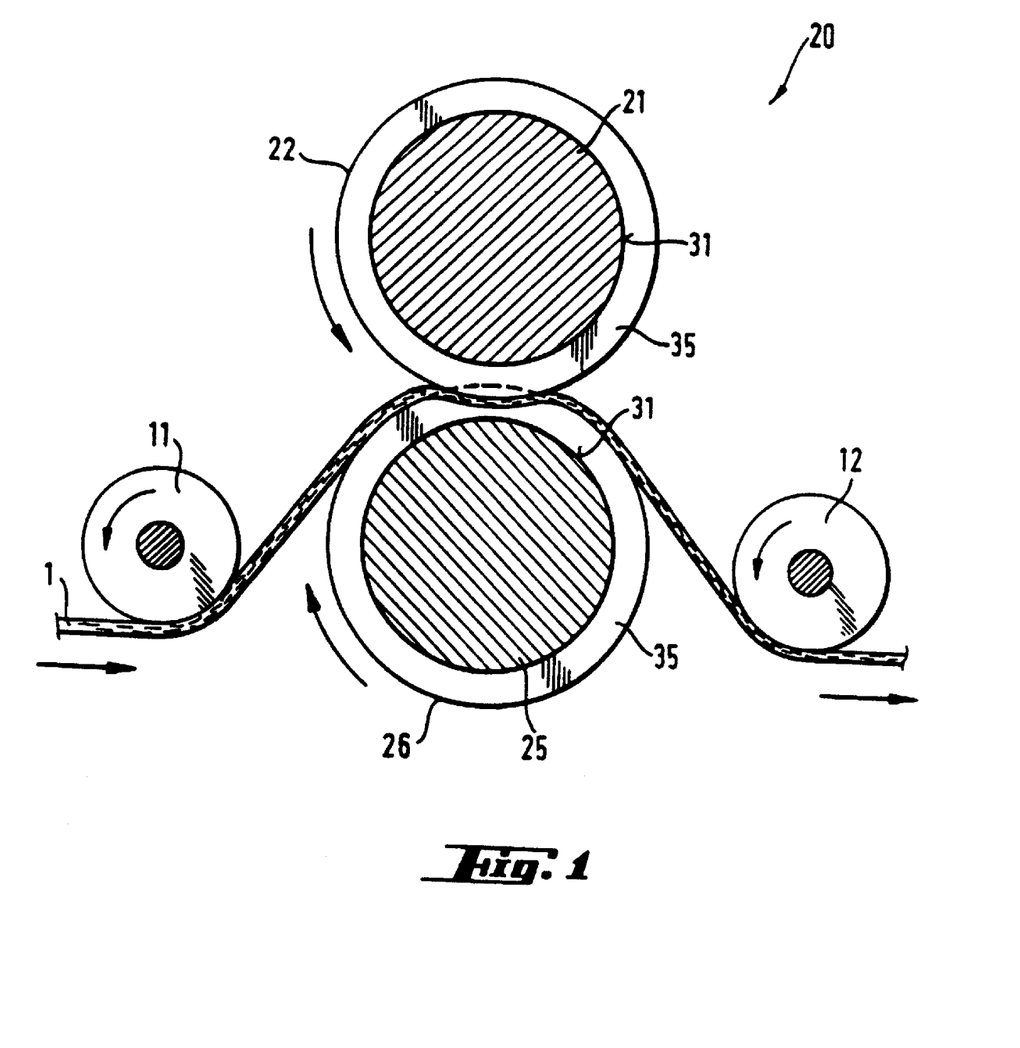
FIG. 1 shows a schematic diagram of an apparatus to be used in a preferred execution of the post formation treatment.
Figure 2:
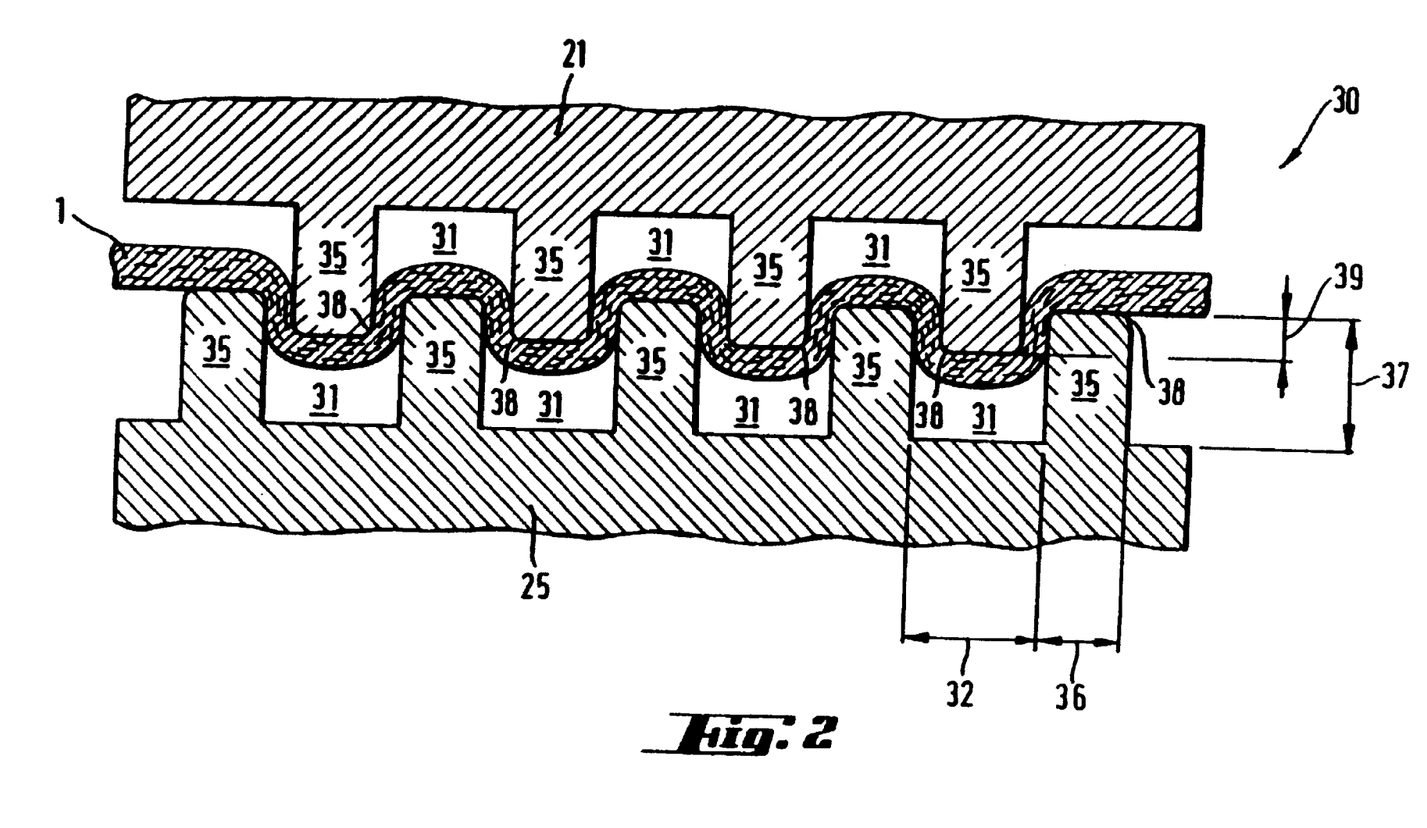
FIG. 2 shows schematically a cross-section through the apparatus.

Referring to FIGS. 1 and 2, the essentially untensioned starting material is directed through an incremental cross-directional web stretching system 20 employing opposed pressure applicators having three dimensional surfaces which at least to a degree are complementary to one another. In a preferred execution, the web 1 is directed by idler rolls 11 and 12 to pass between the ridges and grooves of the surface 22 an uppermost corrugated roll 21 and respective intermeshing grooves and ridges of the surface 26 of the lowermost corrugated roll 25. While the exact configuration, spacing and depth of the complementary ridges and grooves on the uppermost and lowermost corrugated rolls will vary, depending upon such factors as the amount of tensioning desired in the web and properties of the web itself, such as basis weight and resiliency, a specific preferred execution has an essentially rectangular profile as schematically indicated in FIG. 2, whereby—such as for treatment of a web having a basis weight of about 150 gsm and a starting caliper of about 1.5 mm—the grooves 31 have a width 32 of 1 mm, the ridges 35 have a width 36 of 0.6 mm, a distance 37 from bottom of the grooves to peaks of the ridges of about 8 mm, and—both at edges and corners and indicated by 38—smoothed radii of about 0.1 mm. Also indicated in FIG. 2 is the cross-section of the web 1.

For webs having different properties, these dimension should be adopted appropriately, whereby it has been found advantageous to have the width 36 of the ridges 35 to be between 30% and 90% of the width 32 of the grooves 31, preferably between 50% and 70%. The widths of the grooves 31 should be related to the caliper of the treated web, and not be outside the range of 40% to 100% of the caliper, preferably within 60% to 80%.

The degree of overlap 39 of the opposing peaks on the corrugated rolls may of course be adjusted, as desired, to produce more or less strong mechanical treatment in the web.

The maximum overlap 39 is dictated by operational constraints, such as running such an equipment effectively, and by material properties, which might result in perforation or cutting of the web at too strong treatment. It has been found, that this overlap should not exceed 80% of the caliper of the web, preferably be not more than 33% of the caliper of the web, and even more preferably to be not more than 25% of the caliper.

The minimum overlap 39 is defined by the limitation, that the web is actually mechanically treated. This requires, that the distance of the corrugated rolls, which are arranged such that they could intermesh if the distance would be narrowed, is less than the caliper of the web. Then, the "overlap" as used herein, is smaller than zero, and the lower limit of the overlap to be useful for the current invention is about 100%. Preferably, however, the overlap should be more than −15% and more preferably more than +5%. A particularly preferred setting for an overlap to treat a web of 150 gsm and a caliper of 1.5 mm has been found to be +13%.

The materials of the corrugated rolls 21 and 25 can be any suitable material to allow appropriate shaping and to withstand the pressure which the rolls exert to the material, such as metal like aluminium alloys or steel. In case of too low or too high friction between the web and the rolls, the roll surface may be roughened or smoothed or otherwise treated to prevent the web to slip between the corrugation or to not penetrate sufficiently into the corrugations.

It is also recognised that whilst a preferred execution comprises a pair of meshing corrugated rolls having their corrugations aligned substantially parallel to one another, the present invention may also be practised by employing pairs of corrugated rolls wherein the corrugations are not all oriented parallel to one another. Furthermore, the corrugation on such pairs of corrugated rolls need not necessarily be aligned parallel to either the machine. For example, if a curvilinear fluid distribution path be desired, the meshing teeth on the pairs of corrugated rolls employed to incrementally stretch the web may be arrayed in the desired curvilinear configuration to produce adjacent lines along the desired curvilinear contour rather than in a straight line.

Whilst this has been described by referring to one preferred profile 30, other profiles can be used. The grooves and ridges can be in triangular, trapezoidal shape, or more rounded, e.g., in sinusoidal shape, or any other shape allowing intermeshing of two rolls. Obviously, for such arrangements, other preferred dimensions can be readily elaborated for optimal performance.

Whilst a currently preferred execution has uniform arrangement of the ridges and groove both in circumferential and axial direction of the corrugated rolls, specific executions can comprise regions with different patterns, be this in an axial arrangement, e.g., widths of grooves and/or ridges changing across the axial direction of the rolls, or be this in circumferential direction, e.g., the ridges and grooves have a changing depth across the circumference of at least one roll, or at least one of the rolls has an macroscopically curvatured shape, e.g., is thicker in the centre portion than towards the edges.

Also, the use of more than two corrugated rolls can be beneficial, such as when it is helpful to avoid too strong treatment in one step. Thereby, a further roll of the characteristics of roll 25 can be positioned such that its corrugations also intermesh with the corrugations of roll 21. Whilst the corrugations of this roll should be aligned with the ones of the roll 25, the depth of intermeshing can be different or—within the limitations of the alignment—the shape of the corrugations can be different, such as having different radii of the ridges and grooves. Of course, also having more than two rolls can be contemplated, or two sets of pairs of rolls 21 and 25, or other combinations of such set-ups.

In order to further enhance the flexibility of achieving improved performance of the treatment of the web, an additional process step can be included, namely stretching of the web in the direction of the preferential fluid distribution direction. As for the described process, this corresponds to stretching in the longitudinal (machine-) direction of the web. The effect can be the combination of effects according to the present invention with effects such as resulting from treating the web uniformly (i.e., treating all cells in essentially the same way) as described in prior art discussion section.

A further enhancement of the process can be achieved further adding a process step of heating the web, either by a separate process step directly after the post formation treatment as disclosed in the above, or by heating the means that applies the mechanical stress to the web, e.g., one or both of the corrugated rolls. Preferentially, this is applied for webs comprising thermofusible materials (such as the materials comprising thermoplastic fibres). The beneficial effect of this additional heat treatment lies in that the webs can be formed such as to allow relatively easy plastic deformation by the mechanical process, then reaching a desired resiliency and/or strength by the heat curing.

It is further recognised that while the preferred processes herein disclosed employ meshing cylindrical corrugated rolls, the present invention may also be carried out utilising an intermittent stamping operation employing meshing platens to incrementally stretch the web in question.

Without wishing to be bound by the theory, it is believed that the effect of the incrementally elongating process is to create compression zones in the web at the peak point of the corrugations, whereas strain is created in the regions between the peak points. This leads to a modification of pore sizes, pore size distribution and or pore shapes, which is different in these zones.

Such a process has to be contrasted to embossing, whereby only certain regions of the material are compressed and other regions not, and also to the above describe method of stretching a fibrous web, thereby essentially deforming all of the pores in the same way (though at a potentially varying degree). It also needs to be contrasted to conventional creping/microcreping processes, which—whilst having regions with different densities adjacent to each other—have a different orientation (CD or y-direction).

EXAMPLES

The benefits of the present invention are exemplified by applying the post-formation treatment process to two prior art materials and by comparing the improved fluid handling properties both to the one of these materials before the treatment as well as to a number of other prior art distribution materials.

The first starting materials is a wet laid thermally bonded web as explained above having a basis weight of 150 gsm and a density of 0.105 g/cm3, consisting of 45% by weight of chemically-stiffened, twisted cellulose (CS), commercially available under the designation "CMC" from Weyerhaeuser Co., US;

45% by weight of eucalyptus type fibres

10% by weight of CELBOND® from Hoechst Celanese Corporation, US, type 255, lot 33865A, having a dTex of about 3.3, a denier of about 3.0, and a fibre length of about 6.4 mm.

An alternative and even more preferred starting material is a wetlaid chemically bonded web as explained above having a basis weight of 150 gsm and a density of 0.094 g/cm3, consisting of a fibre blend of 90% by weight of chemically-stiffened, twisted cellulose (CS), commercially available under the designation "CMC" from Weyerhaeuser Co., US;

10% y weight of eucalyptus type fibres, bonded by 2% per weight of fibre blend of a polyacrylamide-glyoxal resin markets by Cytec Industries, West Patterson, N.J., USA, under the trade name Parez™ 631 NC.

These have been subjected to the post formation treatment between two rolls at varying overlap depth of the peaks (0.0 mm; 0.2 mm; 0.4 mm) each with a width of a the teeth of 0.6 mm, being 1.0 mm spaced apart.

These materials as well as their untreated references and other comparative examples were subjected the vertical wicking test (see below for details of the method) in machine direction of the web (MD), with measured wicking time to reach 12.4 cm and 8.3 cm as well as respective cumulative flux (table1).

Clearly, the chemically bonded material with an overlap depth of 0.2 mm provides significantly improved performance in both wicking time and flux at 12.4 cm.

The thermally bonded material shows the same direction for improvements, however to a lesser extent.

Table 2 compares for the same materials the wicking times to reach 8.3 cm in CD and MD direction. This time two effects become clear: First, the desired increase in preferential directional distribution as expressed by an increase in the ratio of the CD and MD values. Second an increase in the absolute values in CD direction at high large overlap depth values (0.4 mm) compared to the untreated material.

Test Procedures

Unless specified otherwise, the tests are carried out under controlled laboratory conditions of about 23±2° C. and at 50±10% relative humidity. Test specimen are stored under these conditions for at least 24 hours before testing.

Synthetic Urine Formulation.

Unless specified explicitly, the specific synthetic urine used in the test methods is commonly known as Jayco SynUrine and is available from Jayco

TABLE 1

Vertical wicking test results
Machine direction of material

| Material bonding type | roll overlap (mm) | dry density density | Wicking time [sec] 8.3 cm | 12.4 cm | cumulative flux [ml/sec/cm2] 8.3 cm | 12.4 cm |
|---|---|---|---|---|---|---|
| thermal | 0 | 0.101 | 38 | 116 | 0.126 | 0.065 |
|  | 0.2 | 0.098 | 32 | 101 | 0.147 | 0.077 |
|  | 0.4 | 0.097 | 37 | 102 | 0.123 | 0.067 |
|  | no treatment-reference | 0.105 | 38 | 135 | 0.183 | 0.065 |
| chemical | 0 | 0.092 | 14 | 46 | 0.286 | 0.149 |
|  | 0.2 | 0.097 | 13 | 45 | 0.320 | 0.157 |
|  | 0.4 | 0.093 | 16 | 50 | 0.310 | 0.155 |
|  | no treatment-reference | 0.094 | 20 | 146 | 0.366 | 0.068 |

TABLE 2

Vertical wicking test results
Machine direction (MD)-Cross direction (CD) comparison

| Material bonding type | roll overlap (mm) | Wicking time @ 8.3 cm [sec] MD | CD | ratio CD/MD |
|---|---|---|---|---|
| thermal | 0 | 38 | 46 | 1.21 |
|  | 0.2 | 32 | 50 | 1.56 |
|  | 0.4 | 37 | 54 | 1.46 |
|  | no treatment-reference | 38 | 41 | 1.08 |
| chemical | 0 | 14 | 18 | 1.29 |
|  | 0.2 | 13 | 19 | 1.46 |
|  | 0.4 | 16 | 34 | 2.13 |
|  | no treatment-reference | 20 | 23 | 1.15 |

Pharmaceuticals Company of Camp Hill, Pennsylvania. The formula for the synthetic urine is: 2.0 g/: of KCl; 2.0 g/l of Na2SO4; 0.85 g/l of (NH4)H2PO4; 0.15 g/l (NH4) H2PO4; 0.19 g/l of CaCl2; ad 0.23 g/l of MgCl2. All of the chemicals are of reagent grade. The pH of the synthetic Urine is in the range of 6.0 to 6.4.

Vertical Wicking Test

The vertical wicking test is aiming at evaluating the time required for a fluid front to reach a certain height in a vertical arrangement, i.e., against gravity, as well as amount of fluid picked up by the material during this time.

The principle of this test is to place a sample onto a sample holder equipped with electrodes in form of pins, both functioning to fix the sample in a vertical position and to allow generation of an electrical timer signal. The reservoir of the fluid is positioned on a scale, such that the time dependency of the fluid pick up in the sample resulting from the vertical wicking can be monitored. Whilst not being essential to the test, the test is executed based on a commercially available equipment, the EKOTESTER of Ekotec Industrietechnik GmbH, Ratingen, Germany, which also allowed electronic processing of the data.

Figure 3A:
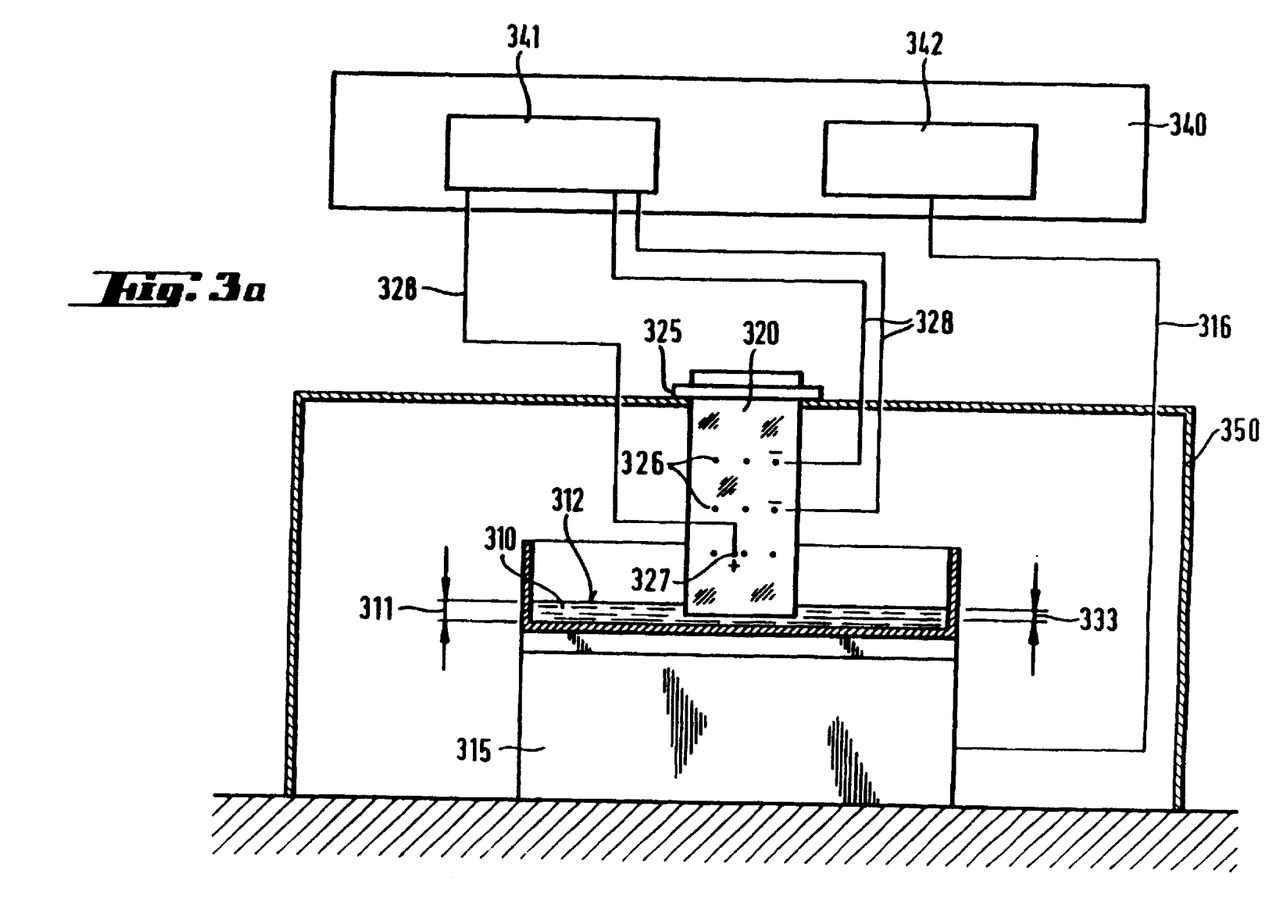
FIGS. 3a) and b) shows the equipment to measure the vertical fluid wicking parameter.
Figure 3B:
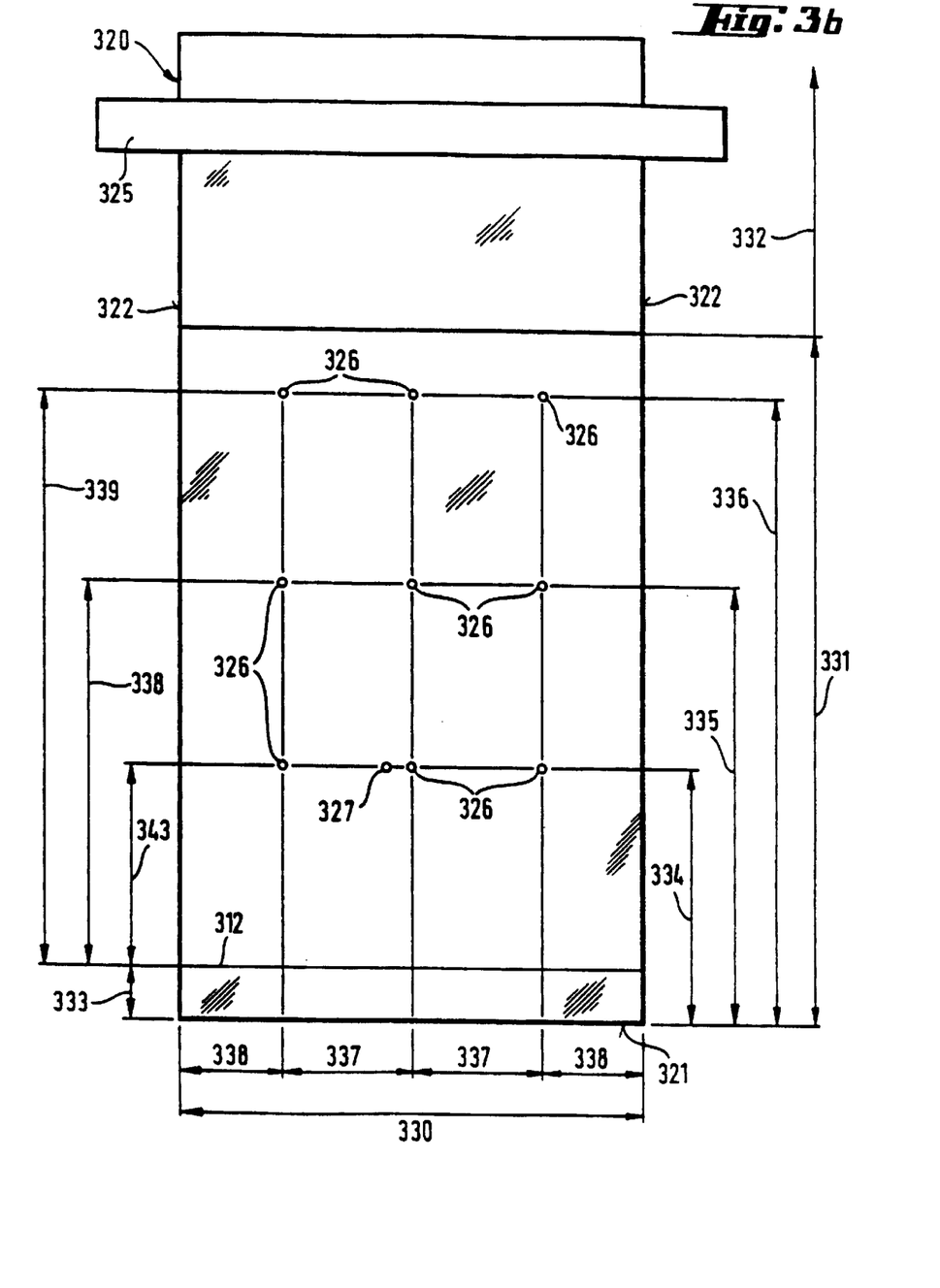

The test set up is schematically depicted in FIGS. 3a and b.

The equipment is essentially made of perspex, and comprises a fluid reservoir (310) to hold 929 grams of test fluid at a liquid level height (311) of 17 mm and a sample holder (320). This reservoir is placed on a scale (315) with 0.1 g accuracy, such as manufactured by Mettler GmbH, type PM3000. Optionally, and indicated through the connection (316), this scale can be connected to an electronic data gathering device (342).

The sample holder (320) is essentially a perspex plate of a width (330) of 10 cm, a length (331) of 15 cm, and a thickness of about 5 mm (not shown). A fixation means (325) is extending beyond these dimensions in the direction (332) which becomes the upward direction during the test to ensure reproducible positioning in exactly vertical direction (i.e., direction of gravity) at a reproducible immersion depth (333) of the bottom edge (321) of the sample holder of 12 mm into the test fluid level in the reservoir (310) during the test. The sample holder (320) is further equipped with 9 cathode electrode pins (326), arranged in three rows in distances (334, 335, 336) of 56 mm, 95 mm, and 136 mm respectively from the bottom edge (321) of the sample holder. There are three electrodes in each of these rows, spaced evenly at distances (337) of 28 mm apart from each other, and the ones located to the longitudinal edge (322) being spaced at distances (338) of 22 mm away from these edges. The electrode pins have a length of about 10 mm, a diameter of about 1 mm, and are slightly sharpened at their end to ease application of the sample. The electrode pins are made of metal. A further anode electrode pin (327) is positioned 5 mm next to the middle cathode electrode pin of the bottom row. The anode (327) and the 9 cathodes (326) are connected (schematically indicated in FIG. 3a) (328) for two cathode pins and the anode pin) to a timing device (341) allowing to monitor the moment when the electric circuit between the anode and the individual cathodes is closed, such as by electrolyte test fluid in a wetted test sample which is positioned between these electrodes.

In contrast to the general procedures outlined above, this equipment is positioned and the test is executed in a temperature controlled hood set at 37° C. and not deviating more than 3° C. The test fluid is also prepared at 37° C. in a temperature controlled water bath for sufficient time to allow constant temperature of the fluid.

The test fluid is filled into the reservoir (310) to have the fluid surface (312) in level with the required height (311), e.g. by adding a predetermined amount of fluid, such as 927.3 gram plus/minus 1 gram.

The test specimen is equilibrated at laboratory conditions (see above), and put into the 37° C. environment just prior to the test. Also prior to the test, the caliper of the sample is measured as outlined below.

The test sample is cut to the size of 10 cm by 15 cm by any convenient means which avoids as much as possible compression effects at the cutting edges, such as with sample cutter such as from JDC Corporation, or sharp cutters like a scalpel or—less preferred—a sharp pair of scissors.

The test specimen is carefully placed onto the sample holder such that the edges coincide with the bottom and side edges (321 and 322) of the sample holder, i.e. such that it does not extend outside the sample holder plate. At the same time, the sample has to be in an essentially flat but unstressed arrangement, i.e., that it should neither form waves, not be in under mechanical tension. Care must be taken, that the sample has only direct contact to the electrode pins and is not contacting the perspex plate of the holder.

The sample holder (320) is then placed in a vertical position into the test fluid reservoir (310), such that the sample holder (320) as well as the test specimen are immersed exactly by a depth (333) of 12 mm into the fluid. Consequently, the electrodes will now have distances (343, 338, and 339) of 44 mm, 83 mm and 124 mm respectively to the fluid level (312), respectively. As the immersion of the sample holder does change the reading of the scale (315), this is tared by an amount predetermined by inserting the sample holder without any sample, e.g. by 6 grams.

It will be acknowledged, that the positioning of the sample holder (320) and the test specimen in a non-tilted arrangement has to be very accurate on one side, but also quick, as the material will start sucking and wicking at first contact with the fluid. A frame (350) into which the sample holder can be readily inserted with the fixation means (325) is also a part of the EKOTESTER, but other means to achieve rapid and non-tilted fixation can be used.

The reading of the scale is monitored as a function of time immediately after positioning of the sample. It has been found advantageously to connect the scale to computerised equipment (340), such as being part of the EKOTESTER.

As soon as the fluid reaches the first row and closes the electrical connection between the anode (327) and the cathodes (326), these times can be recorded by any timing means, the timing unit (341) of the EKOTESTER being a convenient example. Whilst further data processing could be made with each of the three time values of one row, the further data refer to the average of all three electrodes per row, which generally did not spread more than approximately ±5% from the average.

Thus, the data generated are
the time dependent amount of fluid which is picked up by the sample after immersion, and
the time required for the fluid to reach certain heights.
From these, for each of the three heights two important values can be read and reported:

First, the times in seconds until the fluid front reaches the respective heights. Second, the "cumulative flux" for each of the heights, by dividing
the amount of fluid picked up by the sample at the time when this height is reached
by this time
and by the cross-sectional area as defined by the caliper measurement and the 10 cm sample width.

Density/caliper/basis Weight Measurement

A specimen of a defined area such as by cutting with a sample cutter is weighed to at least 0.1% accuracy. Caliper is measured under an applied pressure of 550 Pa (0.08 psi) for an test area of 50 mm diameter. Basis weight as weight per unit area expressed in g/m2, caliper expressed in mm @ 550 Pa pressure, and density expressed in g/cm3 can be readily calculated.

Absorbent Structures and Articles

The fluid distribution materials of the present invention can be utilised in disposable products which are capable of absorbing significant quantities of body fluids, such as urine, perspiration, menses, and water in body wastes. Such articles may be prepared in the form of disposable diapers, catamenial pads, adult incontinence briefs, tampons, and disposable towels and wipes, and the like. The term disposable refers to absorbent articles, which are not intended to be laundered or otherwise restored or reused as an absorbent article, i.e., they are intended to be discarded after a single use, and preferably to be recycled, composted, or otherwise disposed of in an environmentally compatible manner.

In addition to being utilised as a component in disposable articles and products, fluid distribution materials according to the present invention may be utilised alone to comprise an end-use product such as a tissue or towel product, or in combination with various other members or components as part of a wide variety of other products.

The absorbent articles herein generally comprise three basic structural components. One such component is a substantially liquid impervious backsheet. On top of this backsheet is disposed an absorbent core which may itself comprise one or more distinct layers, and which may include a superabsorbent material in one or more of the layers. On top of this absorbent core and joined to the backsheet is a fluid pervious topsheet. The topsheet is the element of the article which is placed next to the skin of the wearer. As used herein, the term "joined" encompasses configurations whereby the topsheet is directly joined to the backsheet by affixing the topsheet directly to the backsheet around the perimeter of the absorbent core, and configurations whereby the topsheet is indirectly joined to the backsheet by affixing the topsheet to intermediate members which in turn are affixed to the backsheet. Preferably, the topsheet and backsheet are joined directly at the absorbent article's periphery by adhesive or other attachment means known in the art. The topsheet may also be adhered to the absorbent core.

A preferred disposable diaper or catamenial pad, for the purpose of this invention comprises an absorbent core; a topsheet superposed or co-extensive with one face of the core, and a liquid impervious backsheet superposed or co-extensive with the face of the core opposite the face covered by the topsheet. Both the backsheet and the topsheet most preferably have a width and length greater than that of the core thereby providing small marginal portions of the backsheet and topsheet which extend beyond the core.

Frequently the backsheet and the topsheet will be fused together in these side marginal portions. The product is preferably constructed in a shaped configuration such as, but not limited to, an hourglass shape.

An absorbent core or absorbent structure according to the present invention comprises or includes a fluid absorbent member as described hereinafter. It should be understood that for purposes of this invention that the term "layers" refers to identifiable components of the absorbent structure, and any structure referred to as a "layer" may actually comprise a laminate or combination of several sheets or webs of the requisite type of materials as hereinafter described. As used herein, the term "layer" includes the terms "layers" and "layered." For purposes of this invention, it should also be understood that the term "upper" refers to the layer of the absorbent core which is nearest to and faces the article topsheet; conversely, the term "lower" refers to the layer of the absorbent core which is nearest to and faces the article backsheet.

It should be noted that the various members, layers, and structures of absorbent articles according to the present invention may or may not be generally planar in nature, and may be shaped or profiled in any desired configuration.

Absorbent structures according to the present invention may include more than one layer or structure having the properties and characteristics attributed herein to the "fluid absorbent member". Such absorbent structures may also include one or more layers having different compositional and functional characteristics, such as acquisition layers and storage layers, to provide functional attributes to augment those of the fluid absorbent members of the present invention and enhance the overall performance of the absorbent structure.

Optionally, a fluid pervious sheet (e.g., a tissue sheet) or other scrim may be positioned between the fluid absorbent member and another component to increase integrity of the fluid absorbent member during processing and/or use. Such sheet or scrim can envelope all or part of the fluid absorbent member only, or simply be positioned as described above without necessarily enveloping the fluid absorbent member. Also, optionally, any layer or structure containing superabsorbent material can be enveloped with a fluid pervious sheet, such as a tissue paper sheet, to obviate user concerns with loose superabsorbent material.

What is claimed is:

1. A fluid distribution material having one preferential fluid distribution direction wherein said material has a wicking time of less than 120 seconds and a cumulative flux of more than 0.075 g/cm2/sec for said preferential fluid distribution direction at a 12.4 cm vertical wicking distance and wherein said material is mechanically treated by feeding the starting material through an incremental cross-directional web stretching system employing opposed pressure applicators having three dimensional surfaces which at least to a degree are complementary to one another.

2. A fluid distribution material according to claim 1 wherein said material has a wicking time of less than 50 seconds and a cumulative flux of more than 0.120 g/cm2/sec for said preferential fluid distribution direction at 12.4 cm vertical wicking distance.

3. A fluid distribution material according to claim 1 wherein the wicking time in said preferential direction is less than 80% of the wicking time in a perpendicular direction for said preferential fluid distribution direction at 8.3 cm vertical wicking distance.

4. A fluid distribution material according to claim 3 wherein the wicking time in said preferential direction is less than 50% of the wicking time in a perpendicular direction for said preferential fluid distribution direction at 8.3 cm vertical wicking distance.

5. A fluid distribution material according to claim 1, having a structure, whereby the structure is essentially sheet like.

6. Fluid distribution material according to claim 1, whereby the fluid distribution is taking place through pores of porous structures.

7. Fluid distribution material according to claim 6 whereby the structure is an open cell foam, consisting essentially of material which allows at least partial permanent plastic deformation upon application of mechanical stress.

8. Fluid distribution material according to any of claim 1 whereby the structure is a fibrous matrix.

9. Fibrous matrix according to claim 8 comprising a mix of at least a first and a second type of fibres, whereby the first type of fibres is stiffer than the second type of fibres, and whereby the second type of fibres has a higher specific surface area than the first type of fibres.

10. Fibrous matrix according to claim 9, whereby the first type of fibre is a high resiliency synthetic fibre.

11. Fibrous matrix according to claim 9, whereby the first type of fibre is a resilient cellulose based fibre, twisted and curled cellulose fibre.

12. Fibrous matrix according to claim 9, whereby the second type of fibre is a high surface area synthetic fibre.

13. Fibrous matrix according to claim 9, whereby the first type of fibre is a high surface area cellulosic fibre.

14. Fibrous matrix according to claim 8 being formed by a wet laying process, and further comprising a binding component.

15. Fibrous matrix according to claim 14, whereby said binding component is a thermoplastic material being mixed into the matrix.

16. Fibrous matrix according to claim 14, whereby said binding component is a chemical binder.

17. Fibrous matrix according to claim 16, whereby the chemical binder comprises polyacrylamide-glyoxal resin.

18. Absorbent structure comprising a Fluid distribution material according to claim 1.

19. A method of using a fluid distribution material, said method comprising providing an absorbent structure according to claim 18 in an absorbent disposable article.

20. A fibrous matrix according to claim 11, whereby the first type of fibre is a chemically stiffened resilient cellulose based fibre, which is a twisted and curled cellulose fibre.

21. Fibrous matrix according to claim 13, whereby the first type of fibre is a high surface area eucalyptus type cellulosic fibre.

* * * * *

UNITED STATES PATENT AND TRADEMARK OFFICE
CERTIFICATE OF CORRECTION

PATENT NO. : 6,294,710 B1
APPLICATION NO. : 09/194253
DATED : September 25, 2001
INVENTOR(S) : Schmidt et al.

It is certified that error appears in the above-identified patent and that said Letters Patent is hereby corrected as shown below:

Column 1
Line 38, please delete "EP0" and insert --EP 0--.

Column 4
Line 13, please delete "[ml/cm2/sec]".

Column 7
Line 11, please delete "No.29" and insert --No. 29--.

Column 12
Line 5, after "material", please insert --1--.
Line 28, please delete "properties," and inset --properties,--.

Column 14
Line 51, please delete "markets" and insert --marketed--.

Column 20
Line 22 (first line of claim 8), please delete "any of".

Signed and Sealed this

Fifth Day of September, 2006

JON W. DUDAS
*Director of the United States Patent and Trademark Office*